United States Patent [19]

Chmurny et al.

[11] Patent Number: 4,810,817

[45] Date of Patent: Mar. 7, 1989

[54] ASPARTYL-BETA SUBSTITUTED PHENYLALANINE DIPEPTIDES

[75] Inventors: Alan B. Chmurny, Frederick; Akiva T. Gross, Rockville; Robert J. Kupper, Mount Airy; Rowena L. Roberts, Derwood, all of Md.

[73] Assignee: W. R. Grace & Co., New York, N.Y.

[21] Appl. No.: 103,984

[22] Filed: Oct. 1, 1987

Related U.S. Application Data

[62] Division of Ser. No. 789,595, Oct. 21, 1985, Pat. No. 4,710,583.

[51] Int. Cl.$^4$ .......................... C07K 5/06; C07K 1/06
[52] U.S. Cl. .......................... 560/40; 560/41; 560/169; 562/567; 562/571
[58] Field of Search ............... 562/567, 571; 560/169, 560/40, 41

[56] References Cited

U.S. PATENT DOCUMENTS

| | | | |
|---|---|---|---|
| 3,475,403 | 10/1969 | Mazur et al. | 260/998.2 |
| 3,492,131 | 1/1970 | Schlatter | 99/141 |
| 3,642,491 | 2/1972 | Schlatter | 99/28 |
| 3,780,189 | 12/1973 | Scott | 426/212 |
| 3,798,204 | 3/1974 | Nakajima et al. | 560/169 |
| 3,871,958 | 3/1975 | Nakazawa et al. | 195/29 |
| 3,920,626 | 11/1975 | Ariyoshi et al. | 560/169 |
| 4,116,768 | 9/1978 | Isowa et al. | 195/29 |
| 4,119,493 | 10/1978 | Isowa et al. | 195/29 |
| 4,165,311 | 8/1979 | Isowa et al. | 260/998.2 |
| 4,256,836 | 3/1981 | Isowa et al. | 435/70 |
| 4,284,721 | 8/1981 | Oyama et al. | 435/70 |
| 4,436,925 | 3/1984 | Isowa et al. | 560/19 |

FOREIGN PATENT DOCUMENTS

| | | |
|---|---|---|
| 0149263 | 7/1985 | European Pat. Off. . |
| 59-3143 | 11/1974 | Japan . |
| WO85/02609 | 2/1985 | PCT Int'l Appl. . |
| 2130216A | 9/1984 | United Kingdom . |

OTHER PUBLICATIONS

Claudio Fuganti et al.—Synthesis of Aspartame vis Asymmetric Hydrogenation of N-Protected (Z)-N-a--L-Aspartyl-$\beta$-Phenylalanine Methyl Ester, *J. Org. Chem.*, vol. 51, pp. 1126-1128, (1986).
Oyama et al., *J. Org. Chem.*, 1981, 46, 4241-5242.
Mazur et al., *J. Amer. Chem. Soc.*, [91:10], 2684-2691, May 7, 1969.
*Chem. Abs.*, 74, 13404n, 1971.
Riphimoff-Felkin et al., *Mem. Pres. Soc., Chim.*, 252-264, (1952), and Translation.
Tou et al., *J. Org. Chem.*, 49, 1135-1136, (1984).
Hamilton et al., *Trends in Biotechnology*, 3, No. 3, pp. 64-68, (1985).
Ulevitch et al., *Bichem.*, 16, No. 24, 5342-5363, (1977).
Schirch et al., *J. Bacteriology*, Jul. 1985, pp. 1-7.
Walsh, *Enzymatic Reaction Mechanisms*, Ch. 25, p. 828 ff, (1979).
Hsiao et al., *Enzymatic Production of L-Serine*, p. 13, (Aug., 1985).
Khan et al., *Tetrahedron Letters*, No. 24, pp. 2649-2655, (1966).
Petkov et al., *Tetrahedron Letters*, 25, No. 34, 3751-3754, (1984).
Isowa et al., *Tetrahedron Letters*, No. 28, 2611-2612, (1979).
Oyama et al., *Enzyme Eng.*, 7, 95-98.
Vogler, *Helv. Chim. Acta*, 33, Fasc. 7, No. 264, 2111-2117, (1950), and Translation.
*J. Amer. Chem. Soc.*, 101, 751, (1979).
*J. Biol. Chem.*, 255, 8234, (1980).
*Biochem. Biophys. Res. Commun.*, 91, 693, (1979).
*Bull. Chem. Soc. Japan*, 51, 271, (1978).

*Primary Examiner*—John Kight
*Assistant Examiner*—Nathan M. Nutter
*Attorney, Agent, or Firm*—Steven T. Trinker

[57] ABSTRACT

Synthesis of phenylserine ester (a) via benzaldehyde and glycine ester using serine hydroxymethyltransferase; and (b) via methyl benzoylacetate. Synthesis of hydroxy-aspartame or derivative by enzymatic coupling of phenylserine or derivative with aspartic acid or derivative. Hydrogenation of the coupled product to give as final product aspartame or analog with related processes and products.

11 Claims, No Drawings

ASPARTYL-BETA SUBSTITUTED PHENYLALANINE DIPEPTIDES

This is a division of application Ser. No. 789,595, filed Oct. 21, 1985 and now U.S. Pat. No. 4,710,583.

FIELD OF THE INVENTION

In its broad aspect the invention involves the preparation of dipeptides and their intermediates, many of which are now compounds. The dipeptide synthesis is accomplished with an effective enzyme and utilizes as one of the reactants a novel group of compounds analogous to phenylserine. Synthesis routes for the latter group are given.

In a preferred embodiment the invention involves the preparation of (2S,3S)-beta-phenylserine ester and the condensation of the ester with blocked-(S)-aspartic acid to make hydroxy-aspartame (a new compound, useful as a sweetener) and certain aspartame homologs and analogs. Several basic stages are involved, each of which has more than one step. Various compositions are made during the course of the overall processes.

For many years aspartame has been produced commercially by coupling Z-aspartic acid with phenylalanine ester. However, phenylalanine is made by fermentation or complex chemical/enzymatic processes and is expensive. Efforts to find a cheaper aspartame process have been long continuing, but, prior to the instant invention, have been unsuccessful. The novel processes herein described are believed to present a cheaper route.

ABBREVIATIONS AND DEFINITIONS

The following are conventional in this art and are used from time to time herein:

Q means a blocking group, e.g., Z (which is carbobenzoxy), as used to block the amine group on L-aspartic acid. Q is further defined in a separate section below.
Me means methyl.
Ph means phenyl.
Phe means phenylalanine.
Z means carbobenzoxy.
Asp means aspartic.
Ser means serine.
APM means aspartame.
BOC (or Boc) means t-butoxycarbonyl.
Lower alkyl means alkyl having 1 to 4 carbons inclusive unless otherwise stated.
Ts means tosyl, i.e., toluenesulfonyl.
DMSO means dimethylsulfoxide.
Metallo-proteinase means proteolytic enzyme having a metal ion at the active center. Examples are those originating from microorganisms such as a neutral protease, originating from actinomycetes and include prolysin, thermolysin, collagenase, crotulus atrox protease; those produced from microorganisms such as *Bacillus subtilis, Bacillus thermoproteoliticus, Streptomyces coespitosus, Bacillus megaterium, Bacillus polymyxa, Streptomyces griseus, Streptomyces naraensis, Streptomyces fradiae, Pseudomonas aeruginosa, Asperillus oryzae, Clostridium histolyticum, Proteus aeruginosa, Aeromonas proteolytica,* and the like. Crude forms are included. For example, the term thermolysin includes crude thermolysin. Other useful enzymes are trypsin, papain, and pronase.

THE Q GROUP

In the synthesis of certain peptides and polypeptides, measures must be taken to prevent the amine group of a given amino acid from reacting with the carboxylic group of another molecule of the same compound (or indeed with the identical molecule). To prevent this, at least one of the reactive radicals has to be blocked. Generally, the amine group on one reactant is chosen, leaving a carboxyl free to react with a free amine group on the other reactant. In the instant case, the amine group on aspartic acid is blocked, leaving adjacent —COOH free to react with amine on phenylserine ester.

Such blocking (or masking or protecting) groups are herein referred to as "Q" groups.

The expedient of the blocking groups was conceived by Emil Fischer in the course of his polypeptide work during the early years of this century, Fischer explored the use of a great many amine blocking groups, and a large number of additional groups have since been suggested. Many of these N-substituents result in a urethane-type group, attached to N, e.g., —NH—C(:O)OR, where R can be alkyl or indeed substantially anything that completes a urethane group. These materials are well known to those skilled in the peptide art. Typical Q radicals are carbobenzoxy (known as benzyloxycarbonyl), p-methoxybenzoxycarbonyl, t-butoxycarbonyl, etc. At the end of the synthesis, Fischer removed the Q group by a simple procedure and peptide syntheses have proceded in analogous manner since Fischer's time. Q removal by specific hydrogenation or the like is an intermediate step in the instant invention and in fact results in formation of a new command.

In the dipeptide art carbobenzoy, $C_6H_5CH_2OCO-$, is so frequently used as a blocking group that it is referred to simply as "Z". It is especially convenient to use in that the group as the acid chloride (carbobenzoxychloride) reacts readily with the amine group in a Schotten-Baumann synthesis, and yet is readily eliminated from the peptide by catalytic hydrogenation, as toluene and carbon dioxide. Other blocking Q groups are readily removable by means well known to those skilled in the dipeptide art. For example, BOC is easily removed by treatment with acid. (See Example 10.)

In general terms Q includes tertiary alkoxycarbonyl groups such as t-butoxycarbonyl (already mentioned), phenylacetyl, acetoacetyl, N-benzylidene, benzoyl, benzyl, t-amyloxycarbonyl; benzyloxycarbonyl groups (including Z, already mentioned), p-methoxybenzyloxycarbonyl; 3,5-dimethoxybenzyloxycarbonyl; 2,4,6-trimethylbenzyloxycarbonyl; p-phenylazobenzyloxycarbonyl; p-toluenesulfonyl; o-nitrophenylsulfonyl; trifluoroacetyl; chloroacetyl; carbamyl; and the like.

Thus Q refers to a conventional group, easily reacted with the amino group of the relevant amino acid, blocking further reaction of that amine group with carboxyl in peptide synthesis, and yet readily removed when the peptide synthesis is over. Accordingly, Q terminology is used in this classical sense, and is not to be construed as limiting the relevant reactants to specific chemically-defined substituents.

SUMMARY OF THE INVENTION

In a major aspect the invention is directed to a process for producing a dipeptide having the formula

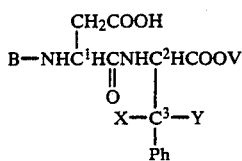

(Formula I)

wherein B represents hydrogen or Q; Q represents an amino acid protective group; V represents hydrogen or an alkyl group having 1, 2, 3, or 4 carbon atoms; $C^1$ and $C^2$ have the common natural configuration of naturally occurring amino acids; and (a) Y is hydrogen and X is HET, where HET represents a hetero-atomic or substituted hetero-atomic group releasable from carbon by reductive cleavage; or
(b) each of Y and X is HET; or
(c) X and Y and $C^3$ together comprise a HET ring or a non-cyclic HET group;

said process comprising:

reacting (i.e., coupling) B-substituted aspartic acid of the formula

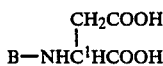

(Formula II)

or a salt (e.g. an acid or an amine salt) thereof with a second amino acid having the formula

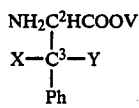

(Formula III)

wherein

X, Y, and V are as defined above and the $C^2$ carbon has the common natural configuration of naturally occurring amino acids;

said reaction being conducted in (d) a water-immiscible solvent in the present of a metallo-proteinase,
(e) a water-miscible solvent in the presence of a non-metallo-proteinase, or
(f) a water-immiscible solvent in the presence of a non-metallo-proteinase.

The above solvent systems include biphasic or multiphase systems (e.g., a solid bound enzyme phase plus water-immiscible organic and aqueous phases), where the enzyme and substrates are dissolved in the aqueous solution and the dipeptide product diffuses to the organic phase.

Certain substituent groups in Formulas I, II, and III are preferred, viz., where:

(a) Y is hydrogen and X is —OR', —SR', —OC(:O)R', —OC(:O)OR, —OC(:O)NHR', —OC(:S)SR, —Cl, —Br, —N₃, —OS(:O)(:O)—R, —S(:O)(:O)—R, —NHR', or —NO₂; or
(b) X and Y are independently —OR', —SR', RS(:O)(:O)—, —OC(:O)R', —NHR', or —Cl; or
(c) Y and X together are =O, —S(CH₂)ₙS—, —S(CH₂)ₙO—, —O(CH₂)ₙO—, =NNHC(:O)NH₂, =NNHC(:O)R', RNHN=, TsNHN=, or =NOH; and R' is H or R; R is alkyl or alkylene having 1, 2, 3, or 4 carbons, aryl, or substituted aryl; n is 1, 2, 3, or 4; and B is Q.

"Substituted aryl" includes groups such as aralkyl, alkaryl, aliphatic-substituted aryls, and the like. "Alkyl" and "alkylene" include substituted alkyls and substituted alkylenes. X and Y are interchangeable.

There are even further substituent preferences, e.g., where:

(a) Y is H and X is —OR', —SR', —OC(:O)R', —OC(:O)OR, —OC(:O)NHR', —OC(:S)SR, or —NHR'; or
(b) X and Y are independently —OR' or —SR'; or
(c) X and Y together are —S(CH₂)ₙS—, —O(CH₂)ₙO—, TsNHN=, =NNHC(:O)NH₂, =NNHC(:O)R', or =NOH.

Of (a), (b), and (c) immediately above, further subgroups are preferred:

(a) Y is H and X is —OH, —NH₂, or —NHR where R is lower alkyl; or
(b) X and Y are independently —OR'; or
(c) X and Y together are —O(CH₂)ₙO—, TsNHN=, =NNHC(:O)NH₂, =NNHC(:O)R', or =NOH.

Thus as species, Formula III would include, without limitation, (a) where Y is H, X is —OH, —Cl, —OCOOPh, —OCOOEt, —OCOOMe, —OMe, —OCH₂Ph, —OC(:O)Me, —OC(:O)Ph, —OC(:O)CH₂CH₂CH₃, —OCH₂CH₃, —OCH₂CH=CH₂, —OC(:O)NHCH₃, —OC(:S)SMe, —OC(:S)SEt, —SMe, —SEt, —SPh, and —OC(:S)S—CH₂CH=CH₂; and
(b) X and Y are independently —OMe or —OEt; and
(c) X and Y together form —S(CH₂)₂S—, —S(CH₂)₃S—, or =NNHC(:O)NH₂.

In one aspect the compositions of Formula III are treated reductively (e.g., by catalytic hydrogenation) prior to coupling. Such reduced products include phenylalanine and phenylserine, especially where the precursor is benzoylglycine.

In the text and claims, "HET" is used to define hetero-atomic or substituted hetero-atomic groups, including groups in ring form (e.g., with $C^3$ forming part of the ring). These terms, which apply to the $C^3$ carbon in compounds described herein, are used in the conventional sense to mean that the immediate substituent is an atom or group other than carbon. For example, a hetero-atom could be —Cl or —Br, and obviously the halogen would be attached only to $C^3$. If the hetero atom is polyvalent (e.g., oxygen, sulfur, or nitrogen), it would normally bridge $C^3$ and some other atom or group, e.g., as in the structure $HC^3$—O-lower alkyl, $HC^3$—S—Ph, or —$C^3$—NH—Ph. The phenyl (or other aryl) group can be substituted, e.g., as in tosyl—, $HC^3$—O—SO₂C₆H₅CH₃. The hetero-atom can also be oxygen alone, as

In lieu of the hydrogen substituent per the above, both the relevant valences from X and Y on $C^3$ may be satisfied by hetero-atomic or substituted hetero-atomic, e.g., MeO—$C^3$—OMe, MeS—$C^3$—SMe, and so on.

Certain polyvalent groups may form a ring with $C^3$. Examples are:

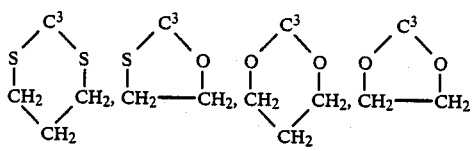

and so on.

With certain groups the $C^3$ attachment is not a ring but a double bond, e.g., $C^3$=NOH, $C^3$=N—NH—tosyl, $C^3$=N—NH—C(:O)NH$_2$, $C^3$=O, and the like.

All of the X:Y groups or atoms are releasable from $C^3$ by one or more of the known methods of cleavage, either before or after peptide coupling. By this is meant, the X:Y compound can be treated in such a way that the atoms or groups are replaceable by hydrogen, leaving $C^3$ as a methylene group, —CH$_2$—. Various methods of reductive cleavage of benzylic substituents are well known to those skilled in the art. The exact nature of the reductive cleavage is dictated by the X:Y atoms or groups present, and the reduction may result in the direct formation of a methylene or may pass through a stable intermediate which is concurrently or subsequently removed, such as C=N—OH→C—NH$_2$→—CH$_2$—. This property is common when X:Y comprise with $C^3$ a multiply-bound oxygen or nitrogen atom. Catalytic hydrogenation is one of the commonest types of reductive cleavage of benzylic functional groups. In fact in this invention all X:Y groups or atoms are replaceable by catalytic methods. For example HC$^3$OMe may be reacted with hydrogen over Pd, Pt, or Raney Ni, and the methoxy group will be replaced by hydrogen. (For a leading reference in this area see Khan, A. M., et al, *Tet. Let.* No. 24, pp. 2649–55 (1966).)

In addition to catalytic hydrogenation certain of the X:Y groups may be reduced by chemical reducing agents to methylenes. For example, halogen or sulfonic acid ester substituents are reduced to methylenes by reaction with NaBH$_4$, NaBH$_3$CN, Zn in acetic acid, MgH$_2$, or n-Bu$_3$SnH, as well as other chemical reducing agents known to those skilled in the art. The only consideration to be made in the choice of a reducing agent is its compatibility with other functional groups in the compound to be reduced. Numerous examples of these reductive procedures are contained in the five-volume reference series *The Compendium of Organic Synthetic Methods*, Ed. Vol. 1 and 2, Harrison and Harrison; Vol. 3, Hegedus and Wade; Vol. 4 and 5, Wade; Wiley-Interscience, New York, N.Y.

As used from time to time herein, the language "treating Q, X, and/or Y groups to replace same with hydrogen" (or equivalent language), is used broadly to encompass processes for removing one or more of such groups and replacing same with hydrogen. As explained in this section, a variety of treatments is available to accomplish this, e.g., acid hydrolysis and various types of reductive cleavage, including catalytic hydrogenation; enzymatic cleavage, chemical reduction, and so on. In some cases different treatments are contemplated for each of the three groups. Certain groups respond preferentially to certain treatments, and guidelines for typical preferences are provided.

In Formula IV (q.v.), where $R^1=R^3$, and in the case where the compound is treated to replace Q with H by acid hydrolysis, the replacement process is not strictly reductive cleavage, but still falls within the general language, "treatment to replace with hydrogen."

Acid hydrolysis is recommended for removal of the following Q groups: t-butoxycarbonyl, phenylacetyl, trifluoroacetyl, acetoacetyl, benzoyl, and t-amyloxycarbonyl. Such treatment results in replacing the group with hydrogen.

Certain Q groups can be removed enzymatically, e.g., phenylacetyl, chloroacetyl, and carbamyl. In such treatment (whereby the group is replaced with hydrogen), procedures well-known in the art may be followed.

In carrying out removal of X, Y, and Q groups (and their respective replacement with hydrogen), addition of acid (e.g., a strong mineral acid) is desirable to depress diketopiperazine formation and to accelerate the rate of removal. The formation of salts facilitates the treatment to replace with hydrogen.

In the basic coupling process, an aspartic acid compound (an amino acid) is reacted with a phenylserine compound (a second amino acid). Both compounds have asymmetric carbon atoms (respectively $C^1$ and $C^2$ in the above formulas), and as such may occur naturally, or may be derivatives of, homologs or analogs of, or otherwise share structural similarities with naturally occurring compounds, where the natural configuration of the amino acids is that given by the Fischer projection,

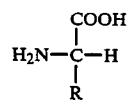

where R is any group that completes the amino acid.

General methods for making the compositions of Formula III are known to those skilled in the art. Typical are the reaction of chlorides with N-protected phenylserine esters, e.g.,

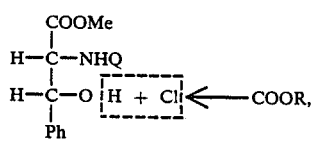

and the like.

Sulfur analogs may require several steps:

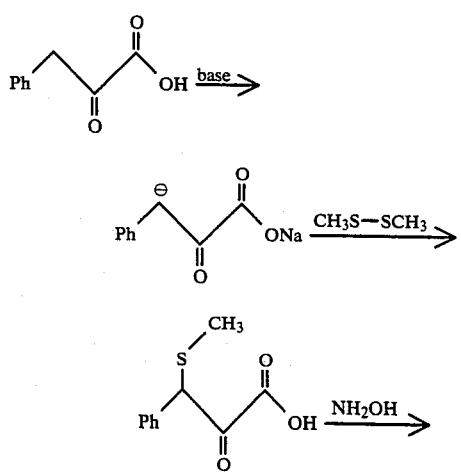

-continued

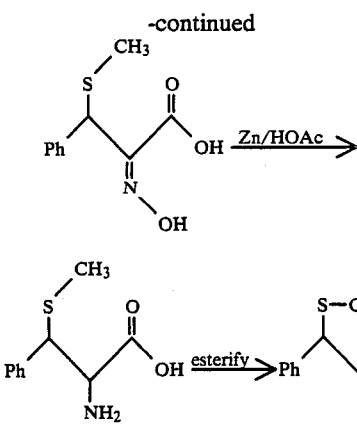

Other modes of synthesis are described in the examles. See especially Examples 14-22.

To complete the process of the invention the dipeptide of Formula I is treated to form a reduced derivative (which may be aspartame); which is to say,

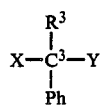

(Formula I, abbreviated)

wherein $R^3 = R^1$ or $R^2$, and $R^1 =$

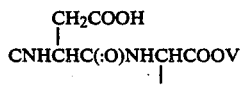

and $R^2 =$

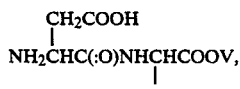

is treated reductively (e.g., by hydrogenation or the like) to form a compound of the formula

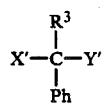

(Formula IV)

wherein at least one of X' and Y' represents respectively X and/or Y as above defined, replaced by hydrogen as a result of the reductive treatment. Where $R^3$ is $R^2$, X' and Y' are both hydrogen, and V is methyl the compound is aspartame, L-alpha-aspartyl-L-phenylalanine methyl ester,

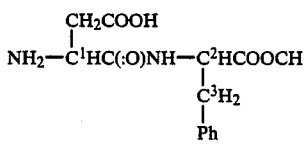

(Formula V)

In the aforesaid reductive process (going from Formula I to Formula IV) new compounds are formed, viz.,

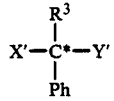

(Formula VI)

in which $R^3$, X', and Y' are as above defined, except that X'—C*—Y' excludes $CH_2$.

Formula VI differs from Formula IV in that Formula VI represents a class of new compounds, and so may not include aspartame, a known compound, which would result when $R^3 = R^2$ and both X' and Y' are H; hence X'—C*—Y' excludes $CH_2$.

BACKGROUND OF THE INVENTION WITH A CONSIDERATION OF CERTAIN PRIOR-ART

It is known to make aspartame by enzymatic coupling of blocked aspartic acid with phenylalanine methyl ester. While the mechanism is undoubtedly complex, the overall result is a simple dehydration, thus:

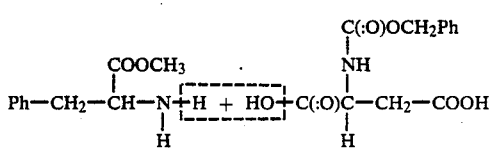

The amine on aspartic acid is blocked with carbobenzoxy (i.e., a "Q" group) to prevent undesirable side reactions.

Aspartame is useful as a sweetener only in the L,L-form, i.e., when its 2 chiral carbons (in this instance one in the phenylalanine moiety and one in the aspartic acid moiety) are in the L form. The 3 other optically-active isomers (L,D; D,L; and D,D) are bitter or tasteless. Procedures using phenylalanine are known that will give the L,L-form substantially free of undesirable isomers.

U.S. Pat. No. 4,284,721, Oyama et al, discloses the foregoing reaction to give the L,L-form, using various immobilized enzymes, including thermolysin. The pores of the immobilized enzyme matrix are filled with water, and thus the reaction of aspartic acid and phenylalanine is carried out in water. The 2 reactants are however dissolved in an organic solvent immiscible with water (e.g., ethyl acetate), and that solution contacts the water-containing immobilized enzyme. Yields of L,L-ZAPM are stated variously as 25.5-88%. The inventors in U.S. Pat. No. 4,284,721 published a parallel paper dealing with the same reaction, reactants, and enzyme, Oyama et al, *J. Org. Chem.*, 1981, 46, 5241-5242, stating, ". . . substrates move from the organic layer to the aqueous layer of the support, where the reaction takes place, and then the product diffuses back to the organic layer effectively . . . " This paper also mentions that in organic solvents "the reaction rate is rather slow as compared with that in aqueous solution." And see Oyama et al, Enzymatic Production of Aspartame, *Enzyme Engineering*, 7, pp. 96-98, disclosing reaction of L-aspartic acid with D,L-phenylalanine to give L,L-aspartame, using thermolysin. The reaction is carried out in water. The reaction product is in the form of an "insoluble addition compound", ZAPM.PheOMe. (See Isowa below.) The Z group is removed by catalytic hydrogenation.

Isewa et al, *Tetrahedron Letters*, No. 28, pp. 2611-2612 (1979), discloses that the thermolysininduced reaction of Z-L-aspartic acid with L-phenylalanine-OMe in water gives Z-L-Asp-L-Phe-OMe-L-PheOMe; which is to say, the L,L-reaction product forms an addition product with the PheOMe reactant. The enzyme was not immobilized. When racemic mixes of reactants were used, only the L,L-aspartame product was precipitated as the addition compound. The phenylalanine portion was separated by use of aqueous hydrochoric acid and the Z group removed by catalytic hydrogenolysis, thereby to give free L,L-aspartame. Yields are high, typically in excess of 90%. Formation of such addition compounds by enzymatic coupling in aqueous media is also described in U.S. Pat. Nos. 4,116,768, 4,119,493, 4,165,311, 4,256,836, and 4,436,925.

Petkov et al, Enzyme Peptide Synthesis, *Tetrahedron Letters*, 25, No. 34, pp. 3751–3754 (1984) teaches reaction of Z-Asp with PheOMe in water using thermolysin. With excess PheOMe an addition compound is formed (per Isowa et al supra). Reaction times of 3–4 hours give excellent yields (typically in excess of 90%).

To summarize certain of the prior art, the reaction of Z-aspartic acid with phenylalanine methyl ester, using immobilized thermolysin:

(a) in water, the reaction is fast, with good yield of an addition compound, Z-L,L-Asp.PheOMe;

(b) in organic solution, the reaction is slower, but no addition compound separates;

(c) whether in water or organic solution, thermolysin forms L,L-aspartame from racemic reactants, i.e., L,D-Phe+L,D-Asp.

In one step of the instant invention methyl 2-oximino benzoylacetate is hydrogenated to make erythro-beta-phenylserine methyl ester. See Example 4. In that connection the following article is of interest.

Elphimoff-Felkin et al, Mémoires Présentés a La Société Chimique (1952), pp. 252–264, at p. 259, disclose hydrogenation of ethyl 2-oximino benzoyl acetate, dissolved in acetic acid, in the presence of $PtO_2$, using hydrogen. They report a mix of threo and erythro isomers of phenylserine, stating that the erythro isomer predominated. A repetition of their work confirms their result, the mix analyzing 75% erythro isomer and 25% threo isomer. The corresponding reaction in the instant invention differs in use of catalyst (Pd metal, not the French $PtO_2$) and in the use of solvent (methanol, not the French acetic acid). These differences result in a yield of essentially pure erythro isomer, and such result was not to be predicted. Using the reference French procedure, 1 g of oxime gives 600 mg of erythro isomer and 200 mg of threo isomer, an overall yield of 92% (based on oxime) and an erythro isomer yield of 54.3%, based on oxime. This compares with yields of 95+% of pure erythro isomer obtained in the invention process, same basis. See Example 4, using methyl ester, and Example 5, using ethyl ester.

DIFFERENCES OVER THE PRIOR ART

Although phenylserine differs from phenylalanine only by having a hydroxyl group instead of a hydrogen, its enzymatic reaction with aspartic acid is startlingly different. As noted, D,L-Phe+L-Asp in water, with enzyme, gives an addition compound; the reaction is fast, the yield good. Substitution of D,L-Phe by D,L-erythro-beta-phenylserine methyl ester, on the contrary, gives a mixture of products, and no addition compound is separable. See Example 9. The art teaches that the reaction in organic media is slower than in water, and one might expect that substitution of phenylserine for phenylalanine would give results even worse than phenylserine+aspartic acid in water. It is surprising, therefore, that phenylserine+aspartic acid in organic media not only gives an excellent yield of Dipeptide I, but proceeds about 2.5 times faster than the corresponding reaction using PheOMe+L-Asp.

International Patent Application No. PCT/HU84/00060 filed 7 December 1984 discloses hydrogenating a phenylserine derivative of the formula

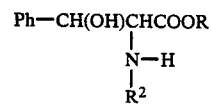

to prepare

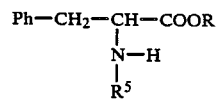

where R is hydrogen or $C_{1-4}$ alkyl, $R^2$ is hydrogen or $—C(:O)R^4$, and $R^4$ is $C_{1-4}$ alkyl, aralkyl, or aryl, and $R^5$ is H or $—CO—R^4$. In several examples D,L-threo-phenylserine is hydrogenated to phenylalanine, and hydrogenation of the erythro-isomer is mentioned.

Tou and Vineyard, *J. Org. Chem.* 1984, 49, 1135–1136, teach conversion of threo-beta-phenyl-L-serine to hydrochloride salt of threo-O-acetyl-beta-phenylserine, which is converted by hydrogenolysis to N-acetyl-L-phenylalanine, followed by hydrogenolysis of the latter to L-phenylalanine.

Japanese Pat. No. 7332830, WPI Acc. No. 75-31430W/19, of Feb. 28, 1979, discloses condensation of glycine and benzaldehyde with threonine aldolase.

PREPARATION OF
(2S,3S)-BETA-PHENYLSERINE ESTER

An Overview

Consider the formula of beta-phenylserine:

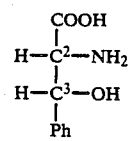

Four stereoisomers are possible and in fact are known: two in the erythro form, comprising the (2S,3S)-configuration and its mirror image, (2R,3R)-; and two in the threo form, (2R,3S)- and its mirror image (2S,3R)-. Two racemic mixes of these four are also known, i.e., the erythro form, (2RS,3RS)-, and the threo form, (2RS,3SR)-. See *Dictionary of Organic Compounds*, pp. 238–239. This use of absolute configuration conforms to the Cahn, Ingold, Prelog convention.

Of the four beta-phenylserine isomers, only the (2S,3S)-form is utilized by the coupling reaction described in Example 8. This isomer can be used either in its pure form, or in the form of the erythro racemic mix, (2SR,3SR)-, or simply (SR,SR), which racemate consists of (2S,3S)-beta-phenylserine and its mirror image, (2R,3R)-beta-phenylserine. Of this racemate (in the ester form) only the (2S,3S)-isomer enters the coupling reaction of Example 8. The reason for this is that the enzyme is selective and will condense only the (S,S)-isomer under the conditions of Example 8. The same is true of the blocked aspartic acid reactant, Q-Asp. (For abbreviations and definitions, see below.) Given the discovery that the S,S-isomer of phenylserine works, one would expect that the 2S,3R)-isomer would also work; but, as above noted, it does not. It is surprising, therefore, that the S,S-isomer works, and that it alone of the four optical isomers works. Indeed, its use is critical. The phenylserine reactant may include the threo-isomer, provided the erythro-isomer is also present.

In Example 8 the beta-phenylserine reactant is the erthro racemate, (2SR,3SR)-, methyl ester, and this preferential product is made by two novel processes, namely:

(A) Condensing benzaldehyde with glycine methyl, ethyl, or propyl ester to give phenylserine ester, using serine hydroxymethyltransferase—herein referred to as the SHMT Process; and (B) Condensing methyl benzoate with an alkyl acetate, converting the condensate to the beta-keto oxime, and reducing the oxime to erythro-phenylserine ester—herein referred to as the Methyl Benzoate Process.

THE SHMT PROCESS

Background

It is known to condensate glycine with formaldehyde to give L-serine using serine hydroxymethyltransferase (SHMT) (also known as serine transhydroxymethylase). See Hamilton et al, Manufacture of L-Amino Acids with Bioreactors, *Trends in Biotechnology*, 3, No. 3, pp. 64–68; and U.K. Patent Application No. 2,130,216A of Nov. 18, 1983. Nakazawa et al, in U.S. Pat. No. 3,871,958, Mar. 18, 1975, disclose the enzymatic condensation of benzaldehyde with glycine to give beta-phenylserine; SHMT is not specified, and whether it was in fact used is uncertain. U.S. Pat. No. 3,871,958 also teaches condensation of benzaldehyde with ethanolamine. So far as can be determined, the reaction of benzaldehyde with a glycine ester using SHMT is novel. In fact, apparently the only reference to glycine ester and SHMT in the literature is Ulevitch et al, Biochemistry, 16, No. 24, pp. 5342–5363 (1977), disclosing cleavage of beta-phenylserine to benzaldehyde and glycine ester. This reaction is of course the opposite of the invention process.

SHMT is readily available. See Schirch et al, *J. Bact.*, 163, No. 1, pp. 1–7 (July 1985); and Ulevitch et al, op. cit.

Considerable confusion exists in the literature and in patents concerning the identity of enzymes catalyzing the reactions described above. Enzymes have been reported with names such as threonine aldolase and allothreonine aldolase. D-specific counterpart enzymes have also been reported. At times these activities have been shown to be the same enzyme, but at other times separate enzymes have been shown to catalyze these reactions. To add to the confusion mammalian cells possess mitochondrial and cytosolic SHMT activities. These enzymes are clearly different, and furthermore the activity of SHMT towards various substrates varies from one mammalian cell type to another.

SHMT and its relatives have been reported in eucaryotes—fungal, plant, and animal cells—and in procaryotes (bacteria). Most of the information on SHMT is based on mammalian cell enzyme. Because large quantities of enzyme are more readily available from a bacterial source, the inventive process has chosen to use SHMT from *Escherichia coli* (*E. coli*). The *E. coli* strains used in the invention as enzyme source were genetically engineered to produce elevated levels of SHMT. SHMT is the product of the *E. coli* glyA gene. This gene was inserted into the tetracycline resistance gene of pBR322, resulting in loss of resistance to this antibiotic in transformant bacteria. The gene is on a 3.3-kilobase Sal I-EcoRI fragment; plasmid is designated pGS29. The plasmid codes for resistance to ampicillin allowing for selection of bacteria transformed with the plasmid. pGS29 was inserted into two *E. coli* host strains—DH2 and HB101.

EXAMPLE 1

Preparation of Beta-phenylserine methyl ester from Benzaldehyde and Glycine Methyl Ester Using SHMT from *E. coli* as Catalyst Cells of DH2/pGS29 grown in complex broth medium were disrupted in phosphate buffer plus pyridoxal-5-phosphate (P-5-P), and this crude extract was used as the SHMT enzyme source. The extract was added to reaction mixtures containing, at initial concentration, 150 millimolar (mM) glycine methyl ester, 100 mM benzaldehyde, and 50 micromolar (mM) P-5-P in phosphate buffer at pH 8.0. Samples were removed from reaction mixtures at 0, 2, and 4 hour intervals of reaction time. The samples were analyzed by high performance liquid chromatography (HPLC) for beta-phenylserine methyl ester. The amount of erythro and threo isomers was also determined by this method.

After 2 hours of reaction 1.48 g/l of beta-phenylserine methyl ester was produced, 83% of which was the erythro isomer. By 4 hours the concentration of beta-phenylserine methyl ester had increased to 2.14 g/l; at this point the erythro isomer represented 82% of the total.

For use in this invention, SHMT requires pyridoxal-5-phosphate (P-5-P), e.g., at 5 mM-5-mM P-5-P per 100 mM benzaldehyde.

Some Variations in the SHMT Process The concentration of the substrates can vary. An operable range of concentration for benzaldehyde is about 10 to 100 mM, with a concentration of about 100 mM preferred. The concentration of glycine ester can be within the range of about 10 to 150 mM. The upper limit is fixed only by the solubility of the ester, which is about 150 mM. It is preferred that the reaction mixture be saturated with glycine ester.

The SHMT may be immobilized, using any of a variety of supports and immobilization techniques well-known to those skilled in the art. In the Example, whole cells were used, but this is not necessary.

In the Example, 0.6 units of SHMT per ml were used. The concentration may be as low as 0.05 units/ml. (A unit of SHMT is equal to that amount of enzyme which catalyzes production of 1 micromole of benzaldehyde per minute from phenylserine.)

The coupling reaction can be carried out at about 10° to 65° C., preferably in the range 30° to 40° C. The reaction mixture should be maintained at a pH of about 6.5-9, preferably 7.5-8. The synthesis can be batch-wise or continuous. In one embodiment the reaction may be carried out in a water-miscible (e.g., methanol) or water-immiscible, organic solvent (e.g. ethyl acetate).

(B) The Methyl Benzoate Process

Turning now to the methyl benzoate route for making beta-phenylserine, in summary, (i) methyl benzoate is condensed with lower alkyl acetate (examplified here with methyl acetate) over sodium, forming methyl benzoylacetate and by-product methyl alcohol. (ii) The former is treated with sodium nitrite to form the oxime, which is then, (iii) hydrogenated to form a racemic mixture (1:1 S,S/R,R) of beta-phenylserine stereoisomers; i.e., beta-phenylserine methyl ester as the erythro racemate.

Steps (i) and (ii) are old in the art; (iii) is carried out in a novel way per this invention. The integrated series of steps (i), (ii), and (iii) as above stated broadly, is believed novel, as are (ii) and (iii) taken together. Thus the invention includes (i)+(ii)+(iii); and (ii)+(iii).

Reference is made to the following schema.

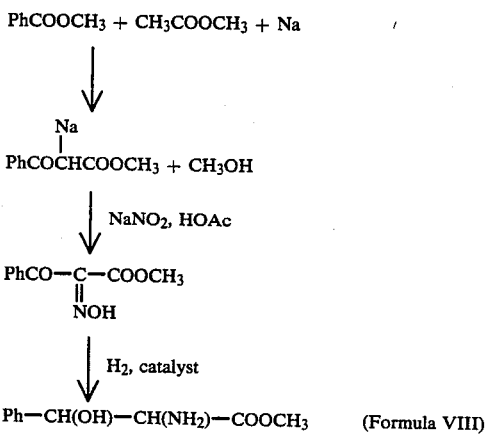

The product of Formula VIII is a racemic mix, i.e., (SR,SR)-phenylserine methyl ester, or erythro-beta-phenylserine methyl ester. This racemate provides the starting reactant for the next stage of the invention, coupling (S,S)-phenylserine ester with Q-aspartic acid, per Example 8. Experimental details for the preparation of erythro-beta-phenylserine methyl ester hydrochloride and its precursors follow.

EXAMPLE 2

Preparation of Methyl benzoylacetate

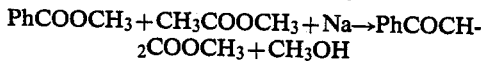

A 1-L flask fitted with a mechanical stirrer, reflux condenser, and nitrogen sweep (to protect the Na), was immersed in a water bath to control temperature (i.e., to provide heat and to cool if need be). In the flask was placed 272.3 g (2 moles) of methyl benzoate; 74.1 g (1 mole) of methyl acetate; 1 gm. atom—23 g., Na; and 32 g (1 mole) of methanol (to react with the Na and to initiate the reaction). The flask was purged with nitrogen and was maintained under a positive nitrogen pressure throughout the reaction. The solution was heated to 80°-85° C. overnight, during which time all the Na metal was consumed. The resulting yellow heterogeneous solution was cooled to room temperature and poured into a separatory funnel containing 130 ml of concentrated hydrochloric acid and 200 g. of crushed ice. This was shaken and the lower aqueous phase removed. (In this step the Na in the Na methyl benzoyl acetate reacts with the HCl and is removed as NaCl.) The residual material was then washed with water, 2×100 mls, saturated NaHCO₃ solution, 2×100 mls, and finally 2×100 mls of saturated brine (NaCl). (By-product methanol leaves with the water in the water washes.) The residual yellow organic phase was then transferred to a distilling flask and fractionated through a 12-inch Vigreux column at 0.5 mm Hg pressure. A forerun containing methyl benzoate and methyl acetoacetate was collected at 37°-42° C. at 0.5 mm Hg. This was followed by a fraction of 82.5 g. methyl benzoyl acetate boiling at 81°-84° C. at 0.5 mm Hg. Yield of the pure product methyl benzoyl acetate based on Na was 46.3%, as a water white liquid.

EXAMPLE 3

Preparation of Methyl 2-oximino Benzoylacetate

Apparatus was a 500-ml flask, fitted with a magnetic stirrer and an addition funnel. In the flask was placed 44.55 g. (250 millimoles) of pure methyl benzoylacetate and 100 ml of glacial acetic acid. This solution was cooled to 10°-12° C. (ice bath) and maintained at this temperature during the addition of 20 g. (290 millimoles) of NaNO₂ dissolved in 35 ml of water. After the addition was complete (30-45 minutes) the solution was allowed to warm to room temperature and stirred for an additional 2 hours, during which time white crystals separated from the solution. The solution was then poured into 500 ml of water and this was filtered. The white filter cake was then washed by 2×100 ml of water and dried to give 48.9 g. of the oxime product, m.p. 134°-136° C. A sample recrystallized from toluene gave white needles, m.p. 135°-136.5° C.

EXAMPLE 4

Preparation of Erythro-beta-phenylserine Methyl Ester Hydrochloride

A 500-ml Parr bottle equipped with shaker was used for the reduction. In the bottle was placed 20.7 g (100 millimoles) of the oxime, 200 ml methanol solvent, 15 ml concentrated HCl and, as hydrogenation catalyst, 500 mg of 5% Pd (metal) on carbon. The bottle was sealed and degassed in vacuo. The shaker was then started and the bottle was maintained at a hydrogen pressure of 15-18 psig by means of a high pressure hydrogen tank feeding into a low pressure tank feeding to the Parr bottle, until hydrogen adsorption ceased (as indicated by a calibrated gauge on the high pressure hydrogen tank). Time required, about 1.75-2.5 hours. The bottle was then vented and degassed in vacuo. Some reaction product solids came out of solution during the hydrogenation, and the bottle was heated to 60° C. to redissolve such solids. Then the hot solution was filtered through a cake of diatomaceous earth (Celite-TM) to remove catalyst. The filtrate was then cooled to 0° C., and glistening silver-white platelets separated. This material was collected by filtration to give 13.6 g of erythro-beta-phenylserine methyl ester hydrochloride product. Concentration of the mother liquor gave another 8.2 g of product. Total yield of material was 21.8 g., or 95.2%; m.p., 168°–169° C. $^1$H NMR (400 mHz) (Free base, CDCl$_3$) δ=1.65 (broad singlet 2H); 3.66 (singlet, 3H); 3.78 (doublet, J=5.78, 1H); 4.92 (doublet, J=5.78, 1H); 7.28 (complex multiplet, 5H). In this run, a suitable H$_2$ pressure is 15–60 psig.

EXAMPLE 5

Preparation of Erythro-beta-phenylserine Ethyl Ester Hydrochloride

The procedures of Example 3 were followed except that the run started with ethyl benzoylacetate, which is commercially available. The corresponding oxime, ethyl ester was prepared as in Example 3 in 97% yield, as fine white needles, m.p. 122.5°–123° C. This oxime was hydrogenated as in Example 4 to give a 94.9% yield of the phenylserine ethyl ester hydrochloride, m.p. 173°–174° C. This was the pure erythro isomer as indicated by NMR. No threo isomer was detected. $^1$H NMR (400 mHz) (Free base, CDCl$_3$) δ=: 1.19 (triplet, J=7.16, 3H) 2.0 (broad singlet); 3.77 (doublet, J=5.70, 1H); 4.10 (doublet of quartets, J=7.16, J$_{gem}$=4.29, 2H); 4.93 (doublet, J=5.70, 1H); 7.29 (complex multiplet, 5H).

These methanol/HCl solutions of substantially pure erythro-beta-phenylserine lower alkyl esters are believed to be novel. They are especially useful as sources of (2S,3S)-beta-phenyl serine lower alkyl esters for reacting with Q-aspartic acid by the process of this invention as hereinafter described.

DIPEPTIDE FORMATION

An Overview

In the next stage of the invention, (S,S)-beta-phenylserine or an ester or analog as above described is coupled with Q-aspartic acid to form a dipeptide, which is then hydrogenated in two steps (or optionally one step) to form aspartame or an analog as the final product.

Aspartic acid has one chiral carbon, thereby providing two optically active isomers. For use in this invention the L-isomer (S-configuration) is required. A mix of L- and D- (S and R) forms can be used, but the L- (i.e., S-) form will be the effective reactant. Z-L-aspartic acid is available commercially and is used preferentially. Unless otherwise stated, "Q-aspartic acid" means the L- (i.e., S-) form.

The coupling process (actually a dehydration) proceeds as follows:

Step 1. Erythro-beta-phenylserine lower alkyl ester (methyl ester is used here as the examplar) is reacted with blocked aspartic acid (with Z as the exemplar block) in organic medium, in the presence of a metalloproteinase as coupling enzyme (immobilized thermolysin is used as the exemplar), thus:

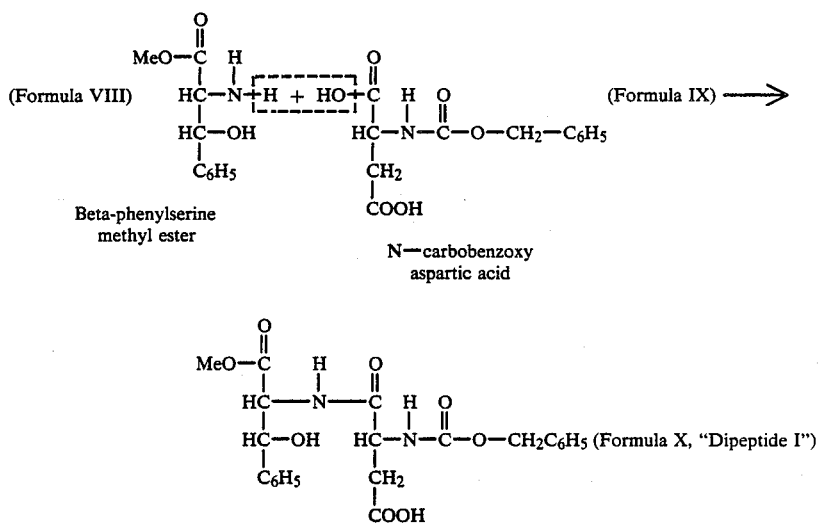

which is N-carbobenzoxy-L-alpha-aspartyl-L-erythro-beta-phenylserine methyl ester. Using absolute configuration, it is N-carbobenzyloxy-(S)-alpha-aspartyl-(2S,3S)-beta-phenylserine methyl ester. In the interests of brevity it will be hereinafter referred to on occasion as "Depeptide I". Dipeptide I is believed novel, as is the class of dipeptides comprising it, where Me is lower alkyl generally and —COOCH$_2$Ph is Q generally. (See Formula XII below.)

In the next step Dipeptide I is catalytically hydrogenated, using Pd on charcoal, under relatively mild conditions, thereby removing the blocking group, Z. The resulting compound is

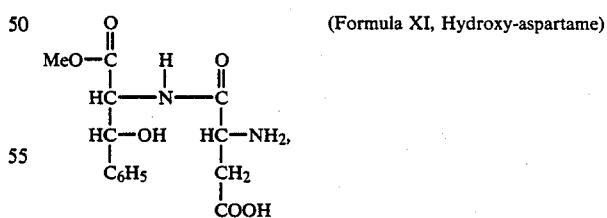

which is L-alpha-aspartyl-L-erythro-beta-phenylserine methyl ester, or hydroxy-aspartame. Using absolute configuration, hydroxy-aspartame is (S)-alpha-aspartyl-(2S,3S)-beta-phenylserine methyl ester. It is useful as a sweetening agent. Hydroxy-aspartame is likewise believed novel. It is immediately useful in the next step, described as follows:

The hydrogenation is continued, at higher temperatures and pressures, thereby to reduce the —OH group on the phenylserine moiety, giving aspartame.

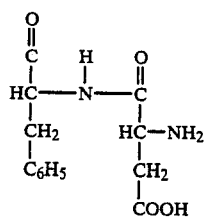

(Formula V, Aspartame)

Aspartame is L-alpha-aspartyl-L-phenylalanine methyl ester.

In one embodiment, the hydrogenation of Dipeptide I is carried through directly to aspartame. Hydroxyaspartame is an intermediate, See Example 13.

Experimental details for the preparation of Dipeptide I will now be given. This preparation involves making precursors, namely immobilized thermolysin and its activation; and preparation of the free phenylserine ester. Data for making immobilized thermolysin and its activation follow the literature and are given here for the sake of completeness.

EXAMPLE 6

Preparation of Immobilized Thermolysin

A polyacrylate resin (3 g), commercially available as Amberlite XAD-7, was washed on sintered glass with ethanol and with a 25 millimolar Tris-HCl buffer, pH 7.5, containing 16 millimolar calcium chloride. "Tris" is an abbreviation for tris(hydroxymethylamino methane). Thermolysin, 750 mg, was dissolved in 15 ml ice-cold 25 millimolar Tris-HCl buffer containing 16 millimolar calcium chloride and 5 molar sodium bromide, pH 7.5. The washed resin was added to the enzyme solution and the mixture was shaken in the cold room at 4° C. for 17 hours. Part of the solution (7.5 ml) was withdrawn and 7.5 ml of 25% glutaraldehyde (crosslinking agent) was added, giving 15 ml of total suspension that was shaken at 4° C. for 3 hours. The thus immobilized enzyme was filtered on a sintered glass and was washed with 0.1 molar Tris.HCl, pH 7.5, containing 5 millimolar calcium chloride and 1 molar sodium chloride, and was washed again with the same buffer except not containing the sodium chloride. The concentration of immobilized enzyme was 50–80 mg/g of wet resin.

A two-phase liquid was prepared in a separatory funnel comprising 50 ml ethyl acetate and 50 ml of 0.1 molar 2(N-morpholino)ethane sulfonic acid at pH 6.0. This mixture was incubated with shaking from time to time for 20 minutes. The phases were separated and the immobilized thermolysin (6 g) was added to the saturated aqueous phase and the mixture was shaken gently at 40° C. for 20 minutes, filtered, and was available for use in Examples 8 and 10. The saturated organic layer was used as the reaction medium in Examples 8 and 10.

EXAMPLE 7

Preparation of Phenylserine Ester Free Base

The coupling reaction of Examples 8 and 10 requires the free bae of phenylserine lower alkyl ester. Therefore the ester hydrochloride of Example 4 is neutralized with base to provide the free ester, as follows. D,L-Erythro-beta-phenylserine methyl ester hydrochloride, 7 g., and sodium carbonate, 3.2 g., in 125 ml water, and chloroform, 200 ml, were shaken in a 500-ml separatory flask. The two phases were separated and the aqueous phase was extracted with chloroform, 2×100 ml; the organic phase was washed with saturated sodium chloride, dried over anhydrous magnesium sulfate, and evaporated to dryness to give a colorless solid of the phenylserine ester, free base. M.p., 100°–101° C.

EXAMPLE 8

Coupling erythro-beta-phenylserine methyl ester with Z-aspartic acid to make Dipeptide I Immobilized thermolysin prepared as in Example 6 (6 g.) was added to a 125-ml Erlenmeyer flask which contained 1.12 g (4.2 millimoles) of Z-aspartic acid and 2.5 g of D,L-erythro-phenylserine methyl ester (12.8 millimoles) in 30 ml saturated ethyl acetate from Example 6. The reaction mixture was shaken at 40° C. for 8 hours in a mechanical shaker. The course of the reaction was monitored by high performance liquid chromatography (HPLC). After 8 hours, according to HPLC, 93% of Z-aspartic acid was consumed. The immobilized enzyme was filtered off and washed with ethyl acetate. The organic phase was washed with 1M HCl, 2×20 ml, and water, 20 ml, then dried over magnesium sulfate. Filtration and evaporation afforded an oil, being Dipeptide I, namely, N-carbobenzoxy-L-alpha-aspartyl-L-erythro-beta-phenylserine methyl ester. (Unreacted phenylserine ester was removed as the hydrochloride in the HCl wash.)

The Dipeptide I oil was dissolved in a minimum amount of chloroform, and then hexane was added until the solution became turbid. The Dipeptide I product crystallized from this solution as slightly colored (yellow) crystals. (The color can be removed if desired by treatment with decolorizing charcoal.) Yield of Dipeptide I, 1.2 g; m.p. 127°–128° C.; $[\alpha]_D^{20} = -7.0°$ (C=1, methanol).

$^1$H NMR (400M Hz) ($\delta$): 2.61 (doublet of doublet, $J_{gem}=17.2$ Hz, $J_{vic}=5.5$ Hz, 1-H), 2.95 (doublet of doublet, $J_{gem}=17.2$ Hz, $J_{vic}=4.4$ Hz, 1-H), 3.49 (singlet, 3-H), 4.51 (multiplet, 1-H), 4.83 (doublet of doublet, $J_{CH-NH}=8.0$ Hz, $J_{vic}=3.6$ Hz, 1-H), 5.02 (singlet, 2-H), 5.07 (doublet, $J_{vic}=3.6$ Hz, 1-H), 6.23 (doublet, J=8 Hz, 1-H), 7.1–7.3 (complex, aromatic 10-H).

$^{13}$C NMR (100.6 MHz) ($\delta$); 36.16 ($CH_2$), 51.01 (CH), 51.74 ($CH_3$), 58.90 (CH), 66.86 ($CH_2$), 73.64 (CH), 125.60, 127.40, 127.82, 128.23, 135.77, 139.36 (C-H aromatics), 155.81, 169.20, 170.86, and 173.22 (C=O).

Mass Spectrum: 445 [(M+H)+], 427 [(M+H—H$_2$O)+].

EXAMPLE 9

Attempted coupling of erythro-beta-phenylserine methyl ester with Z-aspartic acid in water to make Dipeptide I Z-aspartic acid, 534 mg (2 mmol) and erythro-beta-phenylserine methyl ester hydrochloride, 926 mg (4 mmol) were dissolved in water, 12 ml, and the pH was adjusted to 6.2 with 4N NaOH. Thermolysin, 10 mg, was added, and the solution was shaken at 40° C. After 3 hours, some solid precipitated and after 15 hours 2 phases were obtained. The lower phase was extracted with ethyl acetate. Analysis by HPLC showed it contained mainly benzaldehyde. The reaction was discontinued owing to the decomposition of phenylserine into benzaldehyde and glycine Me ester.* *

*At 20° C. the reaction does however proceed to form product, where the ethyl ester is employed.

This failure in water to form an insoluble addition product should be compared to and distinguished from results using phenylalanine.

EXAMPLE 10

Synthesis of N-tert-Butoxycarbonyl-alpha-aspartyl-L-erythro-phenylserine methyl ester The immobilized thermolysin from Example 6 (6 g) was added to a 125 ml Erlenmeyer flask containing 0.5 g (2.1 mmol) of N-BOC-L-aspartic acid and 1.22 g (6.3 mmol) of D,L-erythro-phenylserine methyl ester in 20 ml buffer-saturated ethyl acetate. The reaction mixture was shaken at 40° C. for 10 hours. The product was isolated as described in Example 8. After evaporation of the solvent the product was obtained as a yellowish foam.

$^1$H NMR $\delta$2.7 (doublet of doublet, $J_{gem}=15$ Hz, $J_{vic}=5$ Hz, 1-H), 2.8 (doublet of doublet, $J_{gem}=15$ Hz, $J_{vic}=4$ Hz, 1-H), 3.5 (singlet, 3-H), 3.55 (singlet, 9-H), 4.55 (multiplet, 1-H), 4.85 (multiplet, 1-H), 5.25 (broad singlet 1-H), and 7.15-7.4 (complex, aromatics).

Mass spectrum: 411 [(M+H)$^{30}$], 355 [(M+H-C$_4$H$_8$)$^+$], and 337 [(M+H-C$_4$H$_{10}$O)$^{30}$].

EXAMPLE 11

Hydrogenation of Depeptide I to Make Hydroxy-Aspartame, L-alpha-aspartyl-L-erythro-beta-phenylserine methyl ester In this operation the Z group on the aspartyl moiety of Dipeptide I is replaced with H. Dipeptide I (N-carbobenzoxy-L-alpha-aspartyl-L-erythro-beta-phenylserine methyl ester), 200 mg (0.5 millimoles) is placed in a 15×150 mm test tube. In the test tube is placed 2 mls glacial acetic acid, 0.1 ml (1.2 millimoles) of concentrated HCl, 80 mg of 20% Pd(OH)$_2$ on carbon. This tube was placed in a 500-ml Parr bottle. The bottle was sealed and degassed in vacuo, then purged with 3×25 psig hydrogen. The purged solution was then shaken and pressurized to 45 psig with hydrogen at ambient temperature. An aliquot of the solution was analyzed at 2.5 hours, and this indicated that less than 2% starting material remained. The solution was then filtered and the catalyst cake washed with 2×1 ml of methanol. The resulting filtrate was then concentrated at ambient temperature under high vacuum to give a pale yellow foam. This material was taken up in 1.5 ml of water to give a cloudy solution, which was filtered. The filtrate, a clear pale yellow liquid, pH 2.05, was then adjusted to pH 5.1 with NNaOH. This was done to "neutralize" the HCl salt of the desired product by bringing it to its isoelectric point. At this point the product, hydroxy-aspartame, is an oil. Pure material was obtained by HPLC; or as very fine needles from water/ethanol at pH 5.

Hydroxy-aspartame readily forms salts, e.g., the trifluoroacetate, hydrochloride, hydrobromide, bisulfate, dihydrogen phosphate, and the like.

HYDROXY-ASPARTAME SWEETENER

Consumable products containing hydroxy-aspartame are novel, and part of this invention. This new dipeptide can be incorporated into consumable products in a variety of physical forms, e.g., in powders, tablets, granules, dragees, solutions, suspensions, syrups, emulsions, and the like. They can be used in combination with suitable non-toxic sweetening agent carriers such as water, ethanol, sorbitol, glycerol, citric acid, corn oil, peanut oil, soybean oil, sesame oil, propylene glycol, corn syrup, maple syrup, liquid paraffin, lactose, cellulose, starch, dextrin, and other modified starches; and mono-, di-, and tricalcium phosphate.

Combinations of hydroxy-aspartame with sugar or synthetic sweeteners such as saccharin likewise can be incorporated into the consumable materials in accordance with this invention.

Specific examples of consumable materials containing hydroxy-aspartame are fruits; vegetables; juices; meat products such as ham, bacon, and sausage; egg products; fruit concenrates; powdered beverage concentrates; gelatins; jams; jellies; preserves; milk products such as ice cream, sherbet, and sour cream; syrups such as molasses; corn, wheat, soybean, and rice products such as bread, cereal, pasta and cake mixes; fish; cheese and cheese products; nut meats and nut products; beverages such as coffee, tea; noncarbonated and carbonated soft drinks; beers, wines, and other liquors; confections such as candy and fruit-flavored drops; condiments such as herbs, spices, and seasonings; flavor enhancers such as monosodium glutamate; chewing gum; instant mixes; puddings; and coffee whiteners. Consumable toiletries such as mouthwashes and toothpaste as well as proprietary and nonproprietary pharmaceutical preparations can also be sweetened by hydroxy-aspartame.

The amount of hydroxy-aspartame to be added to the consumable product is the amount which will provide the degree of sweetness desired. This is easily determined by taste tests.

The invention also includes the method of adding hydroxy-aspartame to the consumable products, which is to say, the process of sweetening a consumable product by incorporating thereinto an effective amount of hydroxy-aspartame.

Hydroxy-aspartame can be added to consumables over a wide range of proportions, typically within the range 0.05-3 wt. %. The following list of dosages is provided by way of illustration, and not to state limits.

| Amount of hydroxy-aspartame, Wt % | Consumable |
|---|---|
| 1.3 | Powdered orange beverage concentrate |
| 0.3 | Dietetic syrup |
| 2.4 | Milk pudding powder concentrate |
| 0.09 | Preserves |
| 0.5 | Bottler's cola syrup |
| 0.3 | Gelatin dessert concentrate |

During digestion in the human alimentary tract, hydrox-aspartame and its ester homologs hydrolyze back to the component amino acids, including phenylserine or its lower alkyl eser homolog, as the case may be. Thus the metabolism does not involve a phenylalanine intermediate.

The lower alkyl ester homologs of hydroxy-aspartame are also useful as sweetners and can be used in the same manner as hydroxy-aspartame.

When free hydroxy-aspartame is heated it tends to cyclize with formation of diketopiperazine. In subjecting hydroxy-aspartame to various reactions including replacement of Q groups with hydrogen, hydrogenation, and so, it is generally desirable to carry out the reaction in the presence of acid. Acid stabilizes the hydroxy-aspartame, forming the corresponding salt, and suppresses formation of diketopiperazine. This technique (using HCl) was used in Example 11. In Example 12 the BOC group is removed by acid hydrolysis, using trifluoroacetic acid, hydroxy-aspartame being stabilized as the trifluoroacetate salt. That salt is hydrogenated in methanol-HCl in Example 13.

EXAMPLE 12

Preparation of Hydroxy-aspartame Trifluoroacetate Removal of t-Butoxy Group from t-Butoxy-aspartyl-phenylserine Methyl Ester

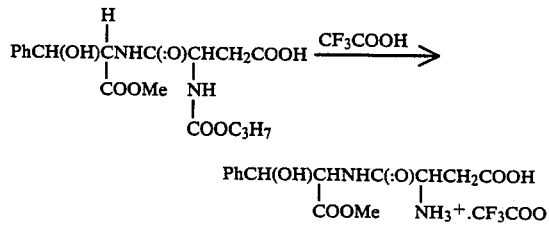

In a 500-ml flask was placed 504 mg (1.2 mmole) of t-butoxy-aspartyl-phenylserine methyl ester and 5 ml of trifluoroacetic acid. This solution was allowed to stand at room temperature for 1 hour. Analysis by HPLC indicated 100% conversion at that point, and the product was isolated by adding 50 ml of ether to the solution and allowing the product to crystallize. This material was collected by filtration and washed with 10 ml of anhydrous ether and dried in vacuo at 56° C. overnight to give 329.6 mg (64.7% yield) of pure hydroxy-aspartame trifluoroacetate. M.p. 155°-156.5° C., with decomposition. $[\alpha]_D^{22} = 20.94$. (C=1.06H$_2$O). Observed rotation = +0.222° ±0.001.

$^{13}$C-NMR (100.6 mHZ) (D$_2$O)$\delta$ = 35.62; 50.13; 53.79; 59.40; 73.52; 117.20 (quartet, $J_{19F-13C}$=291 Hz); 127.34; 129.62; 139.64; 163.76 (quartet, $J_{19F-13C}$=34.9 Hz); 169.21; 171.98; 173.45.

$^1$H-NMR (400 mHz) (DMSO.d$_6$)$\delta$=8.82 (doublet, J=8.0 Hz, 1H); 7.30 (complex multiplet, 5H; 5.97 (broad singlet, 1H); 4.83 (doublet, J=4.3 Hz, 1H); 4.53 (triplet, J=7.5 Hz, 1H); 4.02 (doublet of doublets, J=4.3 Hz, J=8.0 Hz, 1H); 3.56 (singlet, 3H); 3.35 (broad singlet, 3H); 2.71 (two doublet of doublets, J=7.5 Hz, J=17.3 Hz, 2H).

EXAMPLE 13

Reduction of Hydroxy-aspartame Trifluoroacetate to Aspartame

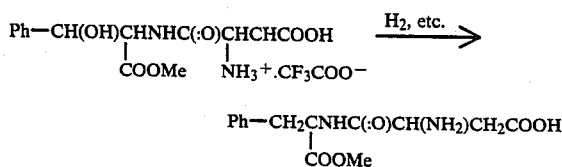

In a 500-ml Parr bottle was placed 10 ml of methanol, 100 mg Pd(OH)$_2$ on carbon, and 212.2 mg (0.5 mmole) of alpha-L-Asp-L-erythroPHSerOME.CF$_3$COOH. To this was added 1 ml of NHCl, and the resulting solution was degassed and purged with 3×25 psig H$_2$. The bottle was then vented and the catalyst filtered from the solution. The solution was then concentrated in vacuo to 1 ml and the pH was adjusted to 5.1 with 6N NaOH. The resulting solution was chilled to 0°-5° C. overnight, and the crystals of aspartame were collected on a Buchner funnel and washed with 0.75 ml of absolute ethanol. After drying in vacuo at 56° C. for 5 hours the pure white crystals of aspartame had a weight of 139.8 mg.

ONE-STEP-HYDROGENATION

As above noted, Dipeptide I (or compounds in the Dipeptide I Class) can be hydrogenated in one step directly to the end product, thereby removing in one operation the Q group on the aspartic acid moiety as well as the hydroxyl group on the phenylserine moiety. The result is the final ester product (aspartame, when alkyl is methyl):

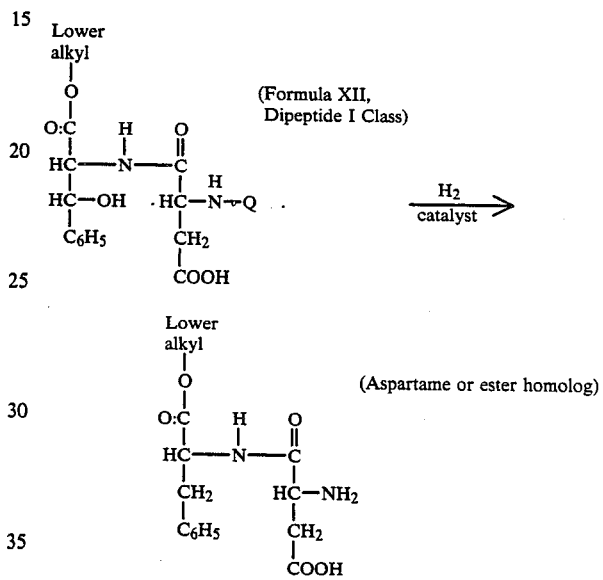

EXAMPLE 14

Hydrogenation of Dipeptide I direct to Aspartame

The procedure of Example 11 was followed except that the hydrogenation solvent chosen was 8.5 ml methanol. 390.9 mg (0.88 millimoles) of Dipeptide I was used, with 1.5 ml NHCl (1.5 millimoles). The Parr bottle was pressured to 60 psig of hydrogen and the solution heated to 45° C. The reaction time was 6 hours. At the end of the reaction the suspension was filtered and the methanol was removed under high vacuum at ambient temperature. The residual material was dissolved in 8 ml of water and the pH was raised from 1.5 to 5.1 with 6N NaOH. The resulting solution was chilled to 0°-5° C. and the aspartame crystallized. Crystals were collected by filtration and washed with 2 ml absolute ethanol. This material was placed in an Abderhalden drying apparatus and dried under high vacuum 0.01 mm Hg) at 56° C. for 24 hours. Yield, 220 mg., 85% M.p., 246°-248° C.

Additional information further explaining the invention follows in Examples 14-22.

EXAMPLE 15

Synthesis of Benzoylglycine

Benzoylglycine, Ph-C(:O)CH(NH$_2$)COOH, can be used as an intermediate in a number of the syntheses for making compounds within Formula III,

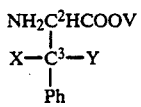

(Formula III)

This intermediate can be synthesized by reduction of lower alkyl esters of 2-oximino-benzoylacetic acid using zinc dust in the presence of acetic acid. The zinc dust (3.85-fold excess) is added gradually to the oxime maintaining a temperature between 45°–50° C. After complete addition of the zinc dust the reaction is stirred for an additional three hours and then filtered to remove the zinc acetate. The product is isolated by concentration of the acetic acid solution.

EXAMPLE 16

Synthesis of the Semicarbazone of Methyl Benzoylglycine

This synthesis is useful when X and Y in Formula III are bound as =NNHC(:O)NH$_2$, =NNHTs, =NNHC(:O)R, or =N—OH.

A 2M aqueous solution of semicarbazide hydrochloride containing 50 mmoles of semicarbazide hydrochloride is added to 50 mmoles of benzoylglycine hydrochloride. Two equivalents of pyridine are added and the solution is warmed gently until the product begins to crystallize. After two hours at room temperature the product is collected by filtration. The semicarbazone of benzoylglycine is dissolved in ethyl ether and a solution, containing one equivalent of 1-methyl-3p-tolyltriazene, is added slowly. The product is isolated by washing the ethereal solution rapidly with hydrochloric acid, then with aqueous sodium bicarbonate and finally dried and concentrated.

EXAMPLE 17

Synthesis of the Ethylene Dithioketal of Methyl Benzoylglycinate

This synthesis is useful when X and Y are connected to C$^3$ as —SCH$_2$CH$_2$S—, or either is —SEt.

Methyl benzoylglycinate hydrochloride is dissolved in an acetic acid solution containing two equivalents of ethanedithio. The reaction mixture is heated to 60° C. and treated with three equivalents of boron trifluoride etherate. After heating for three hours the reaction mixture is left to cool at room temperature overnight. The product, which crystallizes on standing, is isolated by filtration. A similar procedure using two equivalents of ethanethiol is used to prepare the diethylthiol ketal.

EXAMPLE 18

Synthesis of the Methyl Carbamate of Methyl Phenylserinate

The following synthesis is useful when Y is H and X is —OC(:O)NHMe.

The amino moiety of the methyl phenylserinate is protected as the trifluoroacetamide by treating the free amine with one equivalent of ethyl trifluoroacetate. The N-protected methyl phenylserinate is treated with methyl isocyanate to form the corresponding methyl carbamate. The trifluoroacetyl group is removed by treatment with aqueous sodium bicarbonate solution.

EXAMPLE 19

Synthesis of O-Methoxy Carbonyl Derivative of Methyl Phenylserinate

The following synthesis is useful when Y is H and X is —O—C(:O)OMe.

The amino moiety of methyl phenylserinate is protected by treatment with ethyl trifluoroacetate to give the corresponding trifluoroacetamide derivative. The N-protected methyl phenylserinate is dissolved in tetrahydrofuran and treated with methyl chloroformate to form the corresponding O-methoxycarbonyl derivative of methyl phenylserinate. The trifluoroacetyl protecting group is removed by treatment with dilute sodium bicarbonate solution.

EXAMPLE 20

Synthesis of the Xanthate of Methyl Phenylserinate

The following synthesis is useful when Y is H and X is —O—C(:S)—SMe.

The amino moiety of the methyl phenylserinate is protected as the N-t-butoxycarbonyl derivative (BOC) by treating methyl phenylserinate with di-t-butyl dicarbonate in the presence of aqueous sodium bicarbonate. The N-protected methyl phenylserinate is then treated with carbon disulfide and sodium hydroxide to form the corresponding sodium xanthate which is then alkylated directly using methyl iodide. The BOC protecting group is removed by treatment with trifluoroacetic acid.

EXAMPLE 21

Synthesis of the Methyl Ether of Methyl Phenylserinate

The following synthesis is useful when Y is H and X is —OMe.

The amino group of the methyl phenylserinate is protected as the N-t-butoxycarbonyl derivative which can be synthesized as described above. The N-protected methyl phenylserinate is dissolved in tetrahydrofuran at 0° C. and treated with one equivalent of sodium hydride. The resulting alkoxide is alkylated using two equivalents of methyl iodide. The BOC protecting group is removed using trifluoroacetic acid and the product is isolated in the usual manner.

EXAMPLE 22

Synthesis of the Dimethyl Ketal of Methyl Benzoylglycinate Hydrochloride

The following synthesis is useful when X and/or Y is —OMe.

The dimethyl ketal of methyl benzoylglycinate hydrochloride can be prepared by simply dissolving the amino ester in methanol containing 3 A molecular sieves and stirring for 24 hours at room temperature. The molecular sieves are removed by filtration and the product isolated by concentration of the methanol.

EXAMPLE 23

Synthesis of the Methyl Sulfide of Methyl Phenylserinate

The following synthesis is useful when Y is H and X is —SMe.

Phenylpyruvic acid is treated with a strong base to generate the corresponding ketone enolate. The enolate is treated with dimethyl disulfide to form the alpha methyl sulfide which is neutralized and treated with hydroxylamine hydrochloride to produce the oxime. The oxime is readily reduced using a mixture of zinc dust and acetic acid and the carboxylic acid is finally esterified using 3-methyl-1-p-tolyl-triazene.

Note: L-threo-N-acetyl-beta-chlorophenylalanine ethyl ester (i.e., where the amine group is protected by acetyl, Y is H, and X is —Cl) may be prepared as shown in Vogler, *Helv. Chim. Acta,* 33, Fasc. 7, No. 264, pp. 2111-2117 (1950).

Procedures for isolation and recovery of the products made in the foregoing Examples 15-23 are routine. In occasional difficult isolations, resort can be had to standard chromatographic methods.

EXAMPLE 24

Preparation of Beta-Chloro-phenylalanine Ethyl Ester Hydrochloride

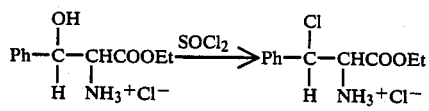

In a 50-ml round bottom flask fit with magnetic stirrer, reflux condenser, and drying tube was placed 2.46 g. (10 mmoles) of beta-phenylserine ethyl ester hydrochloride. The resulting suspension was stirred and heated under reflux until all solid passed into solution (about 2.5-3 hours). The solution was cooled and the reflux condenser was replaced by a still head, and the excess thionyl chloride was removed by distillation. The yellow orange residual oil was then stripped of remaining volatiles at 50° C. under vacuum. The oil was then dissolved in 25 ml of anhydrous ether and allowed to crystallize at 0°-5° C. The product was collected by filtration and washed with 10 ml of anhydrous ether. The pure white solid amounted to 1.78 g. (67.4% yield) as a 1.9 to 1 mixture of erythro and threo isomers (by NMR).

Of the foregoing, Examples 1-14 and 24 are based on actual laboratory work; Examples 15-23 are hypothetical but are believed to work substantially as stated.

Resolution of (SS)- and (RR)-Isomers of Erythro-beta-phenylserine methyl ester In one embodiment the invention is operable to separate and recover the 2 mirror image isomers of erythro-beta-phenylserine methyl ester. The process schema is:

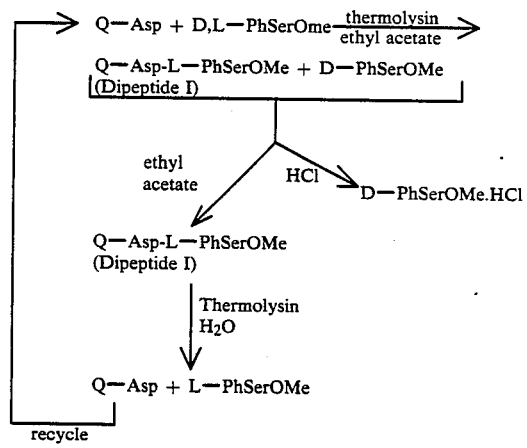

Blocked aspartic acid is coupled with erythro-phenylserine methyl ester as in Example 7. Only the (S,S)-(i.e., L-) isomer of the erythro compound reacts. The reaction product mix thus contains Dipeptide I and free unreacted (RR)- (or D-) erythro isomer. The reaction mix is extracted with ethyl acetate, from which Q-Asp-L-PhSerOMe, Dipeptide I, can be recovered as the hydrochloride. The free (SS)- or L-isomer is obtained by treatment with thermolysin in water. This time, however, the enyzme functions as a hydrolyzing agent, giving back the blocked aspartic acid plus free L-(S,S)-PhSerOMe. To separate the two, HCl is added and the acidified solution is extracted with ethyl acetate to recover Q-Asp. The L-PhSerOMe stays in the acidified solution. The blocked aspartic acid is recycled.

The 2 optical isomers of erythro-beta-phenylserine have uses principally in the pharmaceutical field.

In the above schema, other amino acids, such as Q-phenylalanine can be used in lieu of Q-Asp, and racemates other than D,L-PhSer can be used, e.g., Formula II in the D,L-form.

SOME VARIATIONS

Supports for immobilized enzymes are well-known in the art. They include polyacrylate resins, porous glass beads, hydrophilic gels, vermiculite, and the like.

Suitable organics solvents for the reaction of the 2 substrates (e.g., PhSerOMe and Q-Asp) include a lower alkyl halide such as chloroform or ethylene dichloride; an ester of carboxylic acid, such as ethyl acetate, isopropyl acetate, butyl acetate, and isobutyl acetate; a ketone such as methylisobutyl ketone; and an aromatic hydrocarbon such as benzene, toluene, or a mixture. Other suitable solvents include butanediol, glycerol, dimethylformamide, dimethylsulfoxide, triethylene glycol, acetonitrile, methanol, ethanol, t-butanol, cyclohexanol, dioxane, isopropyl ether, trichloroethylene, tetrachloroethylene, and the like.

In a preferred embodiment protease-catalyzed peptide synthesis is carried out in the presence of water-miscible organic solvent to improve the solubility of reactants and to suppress the ionization of the reacting carboxyl group, resulting in a shift of the equilibrium towards synthesis. Water-miscible organic solvents that can be used are butanediol, glycerol, dimethylformamide, dimethylsulfoxide, triethylene glycol, acetonitrile, and the like. Examples: trypsin in 50% dimethylformamide—see *J. Amer. Chem. Soc.* 101, 751 (1979); 33% dimethylformamide—see *J. Biol. Chem.*, 255, 8234 (1980); papain in ethanol-buffer solution—see *Biochem. Biophys. Res. Commun.* 91, 693 (1979); and prolysin from *B. subtilis var. amyloliquefacieus* in 15% methanol or dioxane—see *Bull. Chem. Soc. Japan*, 51, 271 (1978).

In a biphasic system the enzyme and substrates are dissolved in the aqueous, buffered solution and the product diffuses to the nonpolar organic phase such as benzene, toluene, dichloroethane, tetrachloroethylene, and the like.

Each of the two reactants (Formula II and Formula III, e.g., Q-Asp and PhSerOMe) can be used in a concentration of about 0.01 molar to 1.5 molar, and preferably about 0.1 to 0.5 molar. The mole ratio of Q-Asp:PhSer suitably ranges between 10:1 and 1:10, and preferably between 1:1 and 1:5.

In the catalytic hydrogenation of a dipeptide in the Dipeptide I Class to one in the Hydroxy-Aspartame Class (Formula XI), the hydrogen pressure can be in the range of atmospheric pressure to 1,500 psig and the temperature 0°–150° C. The same pressure and temperature ranges apply in the hydrogenation of dipeptides in Formula XI to aspartame or its homologs, and in the hydrogenation of dipeptides in Dipeptide I Class (Formula X) direct to aspartame or ester homolog. In these hydrogenations the catalyst is suitably Pt or $PtO_2$; or Pd, Pd black, or $Pd(OH)_2$. The suppoert can be carbon, barium sulfate, alumina, or the like. As catalysts, Raney Ni and Raney CO are also useful.

In the coupling reaction, a catalytic amount of enzyme is used, typically 10 mg–3 g of enzyme (dry basis) per millimole of aspartic acid compound in a continuous reactor. In batch runs, the ratio is suitably 10–150 mg of enzyme (dry basis) per millimole of aspartic acid of Formula II, e.g., Q-Asp. As will be evident, in a continuous reactor, at any given pont in time there is a considerable amount of enzyme in the reactor column in proportion to aspartic acid compound. In a batch process this is of course not the case.

The temperature for the coupling reaction is suitably in the range 20°–70° C., and preferably 30°–50° C. The reaction is generally substantially complete in 2–10 hours. If the reaction is unduly prolonged after it is complete, some decomposition may result, with formation of benzaldehyde.

SOME FURTHER CONSIDERATIONS OF NONOBVIOUSNESS

Although the addition of a substituent at the beta position of PheOMe may appear as a minor chemical change, these derivatives behave completely differently from the unsubstituted compound when analyzed as substrates for proteases. For instance, while L-PheOMe is hydrolyzed to L-PheOH by chymotrypsin, papain, and pronase, erythro- and threo-PhSerOMe were not hydrolyzed when these proteases were tried.

The utilization of proteases as catalysts in the synthesis of peptides is well established. This work, however, was involved by and large with the condensation of the common naturally occuring amino acids. So far as is known, the instant invention is the first time that derivatives of the rare amino acid, phenylserine, have been employed in protease-catalyzed peptide synthesis.

Proteases are known to be stereospecific, i.e., they catalyze the specific condensation of the L-isomers, leaving the D-isomers intact. One might expect that the presence of another asymmetric center as in PhSerOMe, however, in a more remote site from the reaction site (beta-position) will not cause any difference in stereoselectivity. The results, however, show that thermolysin is sensitive to the stereochemistry at $C^3$ in compounds of Formula III and in the case of phenylserine methyl ester only the L-erythro isomer is utilized in the condensation reaction.

We claim:

1. An (S)-alpha-aspartyl-(2S,3S)-beta substituted phenylalanine compound of the formula:

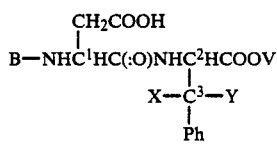

wherein

B represents hydrogen or Q; Q represents an amino acid protective group; V represents hydrogen or an alkyl group having 1, 2, 3, or 4 carbon atoms; $C^1$ and $C^2$ are chiral carbon atoms having an S optical configuration; and Y is hydrogen and X is —OR', —SR', —OC(:O)R, —OC(:O)OR, —OC(:O))NHR', —OC(:S)SR, —Cl, —Br, —$N_3$, —OS(:O)(:O)—R, —S(:O)(:O)—R, —NHR', or —$NO_2$; or X and Y are independently —OR', —SR', RS(:O)(:O)—, —OC(:O)R', —NHR', or —Cl; or X and Y together are =O, —S($CH_2$)$_n$S—, —S($CH_2$)$_n$O—, —O($CH_2$)$_n$O—, =NNHC(:O)$NH_2$, =NNHC(:O)R', RNHN=, TsNHN=, or =NOH;

where R' is H or R; R is alkyl or alkylene having 1, 2, 3, or 4 carbons, or substituted alkyl or substitued alkylene having 1, 2, 3, or 4 carbons; or aryl or substituted aryl; n is 1, 2, 3, or 4; and X and Y are interchangeable.

2. Composition according to claim 1 in which
Y is H and X is —OR', —SR', —OC(:O)R', —OC(:O)OR, —OC(:O)NHR', —OC(:S)SR, —NHR'; or
X and Y are the same or different —OR' or —SR'; or
X and Y together are —S($CH_2$)$_n$S—, —O($CH_2$)$_n$O—, TsNHN=, =NNHC(:O)$NH_2$, =NNHC(:O)R', or =NOH.

3. Composition according to claim 2 in which
Y is H and X is —OH, —$NH_2$, or —NHR, where R is alkyl; or
X and Y are the same or different —OR'; or
X and Y together are —O($CH_2$)$_n$O—, TsNHN=, =NNHC(:O)$NH_2$, =NNHC(:O)R', or =NOH.

4. A dipeptide according to claim 1, having the formula

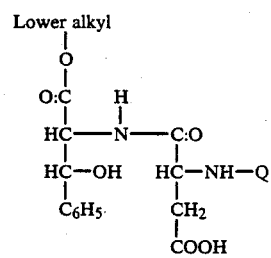

said dipeptide having a configuration L,L- at the alpha carbon atoms.

5. Dipeptide according to claim 4 in which Q is Z, being N-carbobenzoxy-L-alpha-aspartyl-L-erythro-beta-phenylserine methyl ester.

6. A dipeptide according to claim 1, having the formula

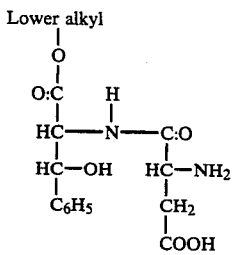

having a configuration L,L- at the alpha carbon atoms, and salts thereof.

7. Dipeptide according to claim 6, L-alpha-aspartyl-L-erythro-beta-phenylserine methyl ester, being hydroxy-aspartame.

8. An (S)-alpha-aspartyl-(2S,3S)-beta substituted phenylalanine compound of the formula:

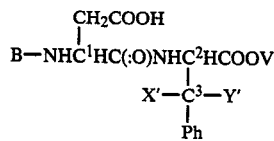

wherein one of X' and Y' represents respectively X and/or Y replaced by hydrogen as a result of treating reductively a compound of the formula:

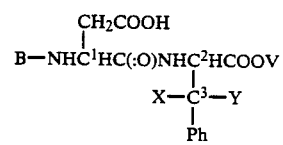

with the proviso that not both X and Y are replaced by hydrogen, and B represents hydrogen or Q; Q represents an amino acid protective group; V represents hydrogen or an alkyl group having 1, 2, 3, or 4 carbon atoms; $C^1$ and $C^2$ are chiral carbon atoms having an S optical configuration; and X and Y are independently —OR′, —SR′, RS(:O)(:O)—, —OC(:O)R′, —NHR′, or —Cl; or X and Y together are $=$O, —S(CH$_2$)$_n$S—, —S(CH$_2$)$_n$O—, —O(CH$_2$)$_n$O—, $=$NNHC(:O)NH$_2$, $=$NNHC(:O)R′, RNHN$=$, TsNHN$=$, or $=$NOH;

where R′ is H or R; R is alkyl or alkylene having 1, 2, 3, or 4 carbons, or substituted alkyl or substituted alkylene having 1, 2, 3, or 4 carbons; or aryl or substituted aryl; n is 1, 2, 3, or 4; and X and Y are interchangeable.

9. Composition according to claim 8 in which B is Q and Q is carbobenzoxy, p-methoxybenzyloxycarbonyl, t-butoxycarbonyl, phenylacetyl, acetoacetyl, N-benzylidene, benzoyl, benzyl, t-amyloxycarbonyl; chloroacetyl, 3,5-dimethoxybenzyloxycarbonyl; 2,4,6-trimethylbenzyloxycarbonyl; carbamyl, p-phenylazobenzyloxycarbonyl; p-toluenesulfonyl; o-nitrophenylsulfonyl, or trifluoroacetyl.

10. Composition according to claim 8 in which X and Y are the same or different —OR′ or —SR′; or X and Y together are —S(CH$_2$)$_n$S—, —O(CH$_2$)$_n$O—, TsNHN$=$, $=$NNHC(:O)NH$_2$, $=$NNHC(:O)R′, or $=$NOH.

11. Composition according to claim 10 in which X and Y are the same or different —OR′; or X and Y together are —O(CH$_2$)$_n$O—, TsNHN$=$, $=$NNHC(:O)NH$_2$, $=$NNHC(:O)R′, or $=$NOH.

* * * * *